(12) United States Patent
Zu et al.

(10) Patent No.: US 9,011,912 B2
(45) Date of Patent: Apr. 21, 2015

(54) EXTENDED-RELEASE ORAL DOSAGE FORMS FOR POORLY SOLUBLE AMINE DRUGS

(75) Inventors: Yanming Zu, Highland Mills, NY (US); Sudhir Gorukanti, Harriman, NY (US); Salah Uddin Ahmed, New City, NY (US)

(73) Assignee: Abon Pharmaceuticals, LLC, Northvale, NJ (US)

( * ) Notice: Subject to any disclaimer, the term of this patent is extended or adjusted under 35 U.S.C. 154(b) by 0 days.

(21) Appl. No.: 12/900,205

(22) Filed: Oct. 7, 2010

(65) Prior Publication Data
US 2012/0087979 A1    Apr. 12, 2012

(51) Int. Cl.
| | | |
|---|---|---|
| *A61K 9/22* | (2006.01) | |
| *A61K 31/445* | (2006.01) | |
| *A61K 31/55* | (2006.01) | |
| *A61K 31/519* | (2006.01) | |
| *A61K 31/18* | (2006.01) | |
| *A61K 9/50* | (2006.01) | |
| *A61K 9/24* | (2006.01) | |
| *A61K 9/28* | (2006.01) | |
| *A61K 9/48* | (2006.01) | |
| *A61K 31/4353* | (2006.01) | |
| *A61K 31/551* | (2006.01) | |

(52) U.S. Cl.
CPC .............. *A61K 9/5078* (2013.01); *A61K 9/209* (2013.01); *A61K 9/2866* (2013.01); *A61K 9/2886* (2013.01); *A61K 9/4866* (2013.01); *A61K 9/5047* (2013.01); *A61K 31/18* (2013.01); *A61K 31/4353* (2013.01); *A61K 31/445* (2013.01); *A61K 31/519* (2013.01); *A61K 31/551* (2013.01)

(58) Field of Classification Search
None
See application file for complete search history.

(56) References Cited

U.S. PATENT DOCUMENTS

| | | |
|---|---|---|
| 5,051,262 A | 9/1991 | Panoz et al. |
| 5,705,190 A | 1/1998 | Broad et al. |
| 6,165,506 A | 12/2000 | Jain et al. |
| 6,287,599 B1 | 9/2001 | Burnside et al. |
| 6,436,441 B1 | 8/2002 | Sako et al. |
| 6,514,531 B1 | 2/2003 | Alaux et al. |
| 6,811,794 B2 | 11/2004 | Burnside et al. |
| 7,008,640 B2 | 3/2006 | Watanabe et al. |
| 2002/0150616 A1 | 10/2002 | Vandecruys |
| 2004/0062800 A1 | 4/2004 | Burnside et al. |
| 2004/0109890 A1 | 6/2004 | Sugimoto et al. |
| 2005/0048119 A1* | 3/2005 | Nangia et al. ................. 424/473 |
| 2005/0208132 A1* | 9/2005 | Sathyan et al. ............... 424/468 |
| 2005/0260263 A1 | 11/2005 | Hsiao et al. |
| 2007/0190145 A1 | 8/2007 | Venkatesh et al. |
| 2007/0196491 A1 | 8/2007 | Venkatesh |
| 2008/0069878 A1 | 3/2008 | Venkatesh et al. |
| 2008/0299188 A1 | 12/2008 | Appel et al. |
| 2008/0311195 A1 | 12/2008 | Sakuragi et al. |
| 2009/0232885 A1 | 9/2009 | Venkatesh et al. |
| 2009/0258066 A1 | 10/2009 | Venkatesh et al. |
| 2010/0159010 A1 | 6/2010 | Kudsi et al. |

OTHER PUBLICATIONS

Hardung, Hendrik; Djuric, Dejan; Ali, Shaukat. Combining HME & Solubilization: Soluplus—The solid soution. Drug Delivery Technology, Apr. 2010, vol. 10, No. 3.*
Technical Information for Soluplus®, BASF SE, Care Chemicals Division, Pharma Ingredients & Services, (Nov. 2009).
Experimental Data Conducted by Applicant, Nov. 2014.

* cited by examiner

*Primary Examiner* — Susan Tran
*Assistant Examiner* — Jessica Worsham
(74) *Attorney, Agent, or Firm* — Fanelli Haag & Kilger PLLC

(57) ABSTRACT

Oral dosage forms for poorly soluble amine drugs are provided. Such dosage forms include an ionizable compound such as an organic acid, an amphiphilic polymer and a release rate-controlling membrane. Such dosage forms allow for the consistent release of the active agent in both gastric pH conditions and in the intestine. Methods of making such dosage forms are also provided.

7 Claims, 6 Drawing Sheets

EXTENDED-RELEASE ORAL DOSAGE FORMS FOR POORLY SOLUBLE AMINE DRUGS

FIELD OF THE INVENTION

The present invention relates to oral dosage forms for poorly soluble amine drugs.

BACKGROUND OF THE INVENTION

It is well understood that solubility of therapeutic agents in physiological fluids is a prerequisite for absorption in the gastrointestinal tract and that weak bases are soluble in gastric pH. Poorly soluble basic active compounds tend to dissolve in the stomach but may precipitate at a higher pH, as in the intestine, or result in dangerously high $C_{max}$ levels of the active compound.

Several strategies have been adopted in an attempt to address such problems. These include (a) co-administration of an ionizable compound that promotes solubility in situ in the intestine and (b) use of a sustained release coat to protect the poorly soluble basic drug from rapid dissolution in the stomach.

However, such attempts have not been entirely successful and have a tendency (a) for acid compounds to react with the drug substance or base resulting in the formation of salts; (b) for acid interaction to result in other types of incompatibility between the dosage form and the active agent; and (c) when released intact in the gastrointestinal tract to create hyperacidity which may cause gastric upset, or after long term use, ulceration.

SUMMARY OF THE INVENTION

The present invention provides oral dosage forms for poorly soluble amine drugs that overcome the problems characterizing previous dosage forms. Such dosage forms may include an ionizable core, an amphiphilic polymer, a poorly soluble amine active pharmaceutical ingredient ("API") and a rate-controlling membrane coating.

Embodiments of the present invention provide a solid dosage form for oral administration that comprises an ionizable compound used as a core which is coated with the following: (a) a barrier layer with or without release rate-controlling properties; (b) a mantle which includes a matrix of API and amphiphilic polymers, wherein such matrix may be prepared by dispersing the API and a solubilizer in a solvent in appropriate proportions; and (c) a release rate-controlling layer wherein the substrate comprises a permeable membrane which includes hydrophobic and hydrophilic polymers, and a plasticizer.

The present invention also includes methods of making dosage forms for poorly soluble amine drugs.

DETAILED DESCRIPTION OF THE INVENTION

The present invention provides oral dosage forms for poorly soluble amine drugs and methods of making such dosage forms that unexpectedly overcome the problems characterizing previously described dosage forms.

It has been unexpectedly discovered that the combination of an ionizable compound with an amphiphilic compound provides greatly enhanced solubility of a poorly soluble amine compound. It has also been unexpectedly discovered that the solubility of poorly soluble amine compounds may be further enhanced when the amphiphilic compound has a hydrophilic-lipophilic balance ("HLB") greater than about 7.0.

In certain embodiments the amphiphilic polymer may have an HLB above about 8.0 or 9.0 or 10.0. In additional embodiments the amphiphilic polymer may have an HLB above about 12.0, 14.0, 16.0, 18.0 or 20.0.

Figure 1:
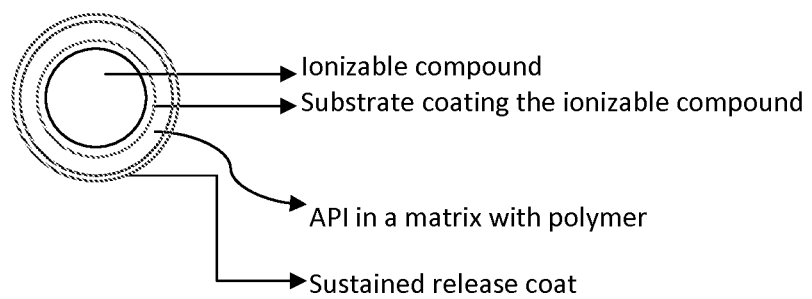
FIG. 1 is a schematic of a representative dosage form according to the present invention.

As shown in FIG. 1, in a representative embodiment of the present invention, the oral dosage form may include (1) an ionizable compound, (2) an amphiphilic polymer, (3) an API and (4) a rate-controlling membrane.

In certain embodiments the ionizable compound may include an organic acid. As shown in Table 1 below, such organic acids may include, for example, citric acid, tartaric acid, fumaric acid, maleic acid, succinic acid, carbomer (polyacrylic acid), phthalic acid, methacrylic acid-ethyl acrylate copolymer, methacrylic acid-methyl methacrylate copolymer, hydroxypropyl methylcellulose phthalate or combinations thereof.

TABLE 1

| Organic Acid | pKa |
| --- | --- |
| Citric Acid | 3.13, 4.76, 6.40 |
| Tartaric Acid | 2.98 |
| Fumaric acid | 3.03 |
| Maleic acid | 1.92, 6.27 |
| Succinic Acid | 4.16, 5.61 |
| Carbomer | 6.0 |
| Phthalic acid | 2.95, 5.41 |
| Poly-(methacrylic acid, methyl methacrylate) 1:1 polymer [Eudragit L] | 6.0 |
| Poly-(methacrylic acid, methyl methacrylate) 1:2 polymer [Eudragit S] | 6.0 |
| Hydroxypropyl methylcellulose phthalate | 5.5 |

In certain embodiments the ionizable compound has a pKa less than or equal to about 6.0.

In certain embodiments the ionizable core may be coated with a barrier membrane which serves as a physical barrier preventing the interaction of the core with the API. This barrier may be coated onto the core by fluid-bed coat or by other suitable means. The composition of the barrier coat may include an ionizable compound release rate-controlling agent such as ethyl cellulose and hydroxypropyl methylcelluose. Such barrier membranes may be used to regulate the availability of an organic acid for the API during the dissolution process, which, in certain embodiments of the present invention, may improve the bioavailability of the poorly soluble amine drug. Such barrier membranes also reduce the risk of dose dumping of the ionizable core and the side effects associated therewith, such as gastro-intestinal upset, or after chronic use, ulceration. Such barrier membranes also may lower the risk of dose dumping of the API and side effects associated therewith, such as high $C_{max}$.

Certain embodiments of the present invention also may include a mantle which may comprise an API in an amphiphilic polymer. Such mantle may be coated on the barrier layer described above. The mantle may be prepared by dispersing an API and an amphiphilic polymer in an appropriate solvent and spray-coating the dispersion onto the core.

In certain embodiments the amphiphilic polymer may include polyethylene glycol 6000/vinylcaprolactam/vinyl acetate 13/57/30 (SoluPlus®), d-α-tocopheryl polyethyleneglycol 1000 succinate (Vitamin E-TPGS), poloxamer (Pluronic®) or combinations thereof. In certain embodiments the amphiphilic polymer may have a molecular weight greater than about 50,000 Da. The amphiphilic polymer also may have an HLB greater than or equal to about 7.0.

According to certain embodiments of the present invention, the API may have a molecular weight less than about 550 Da, preferably less than about 500 Da. The nitrogen content of the API in certain embodiments may be from about 3% to about 23%, and in other embodiments from about 8% to about 15%. In certain embodiments the API may have a pKa from about 5 to about 11 and in other embodiments from about 8 to about 9. Table 2 provides a non-limiting list of representative poorly-soluble amine APIs.

TABLE 2

| Amine Drug | Molecular Weight | Nitrogen Content (% of mol. Wt.) | pKa |
|---|---|---|---|
| Paliperidone | 426.484 | 13.13 | 8.2, 8.6 |
| Donepezil | 379.492 | 3.7 | 8.9 |
| Tamsulosin | 408.48 | 6.85 | 8.37, 10.23 |
| MethylPhenidate | 233.31 | 6 | 8.9 |
| Olanzapine | 312.439 | 17.92 | 5, 7.4 |
| Dipyridamole | 504.626 | 22.1 | 6.4 |

In certain embodiments the mantle may be coated with a drug release rate-controlling membrane. Such membranes include, but are not limited to, hydrophobic polymers such as ethylcellulose, methylcellulose, propylcellulose, ethylmethylcellulose, cellulose acetate, cellulose acetate propionate or ethyl acrylate and methyl methacrylate copolymer, and optionally include enteric polymers such as methacrylic acid-ethyl acrylate copolymer, methacrylic acid-methyl methacrylate copolymer, hydroxypropyl methylcelluose phthalate and hydroxypropyl methylcellulose acetate succinate, hydrophilic polymers such as hydroxypropyl methylcellulose, hydroxypropyl cellulose, povidone, copovidone, and plasticizers such as polyethylene glycol, triacetin, dibutyl sebacate, triethyl citrate, or combinations of any of the above.

Figure 2:
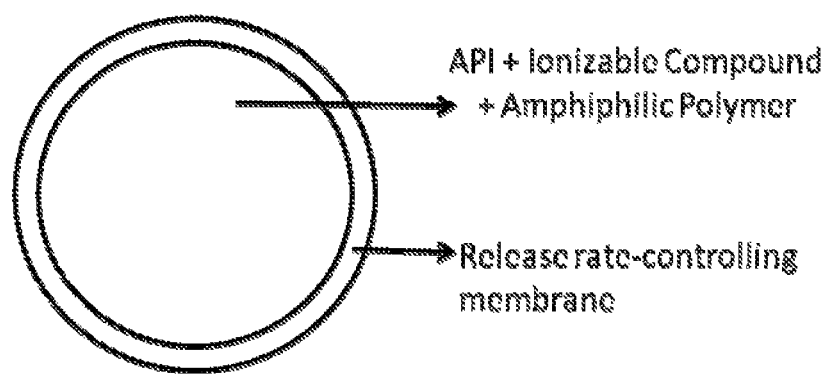
FIG. 2 is a schematic of a second representative dosage form according to the present invention.

In another representative embodiment, a release controlling membrane may coat an admixture of an API, an ionizable compound and an amphiphilic polymer (See FIG. 2).

Figure 3:
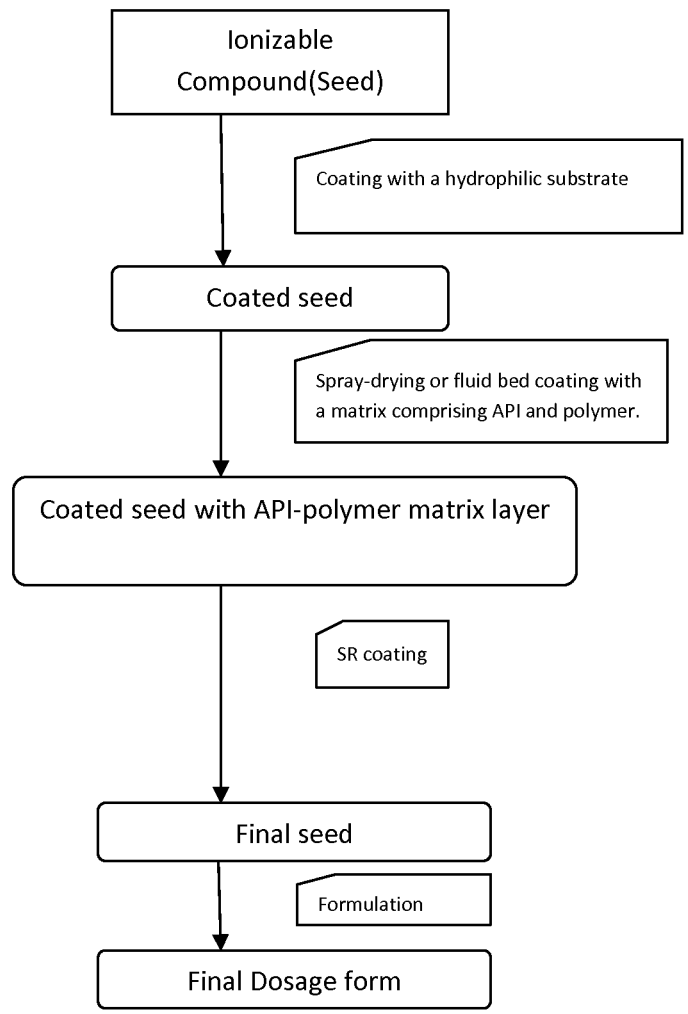
FIG. 3 provides a representative flow chart for making oral dosage forms according to the present invention.

The present invention also includes methods of making oral dosage forms described above. A representative method is illustrated in FIG. 3. Such methods may include the use of an ionizable compound as a starting material or seed. In certain embodiments the coated seed may be coated by a hydrophilic substrate. In other embodiments the coated seed may be coated by a hydrophobic and hydrophilic substrate to control the release rate of the ionizable compound.

In certain embodiments the seed (or coated seed) may be coated with a matrix comprising an API and an amphiphilic polymer. The next step may include the application of an SR coating to form an extended-release oral dosage form for poorly soluble amine drugs. As used herein "extended-release" refers to an oral dosage form that allows for the prolonged or delayed release of an active agent as compared to an immediate release dosage form. For example, an extended-release dosage form may be capable of being administered once or twice daily rather than more frequently.

Figure 4:
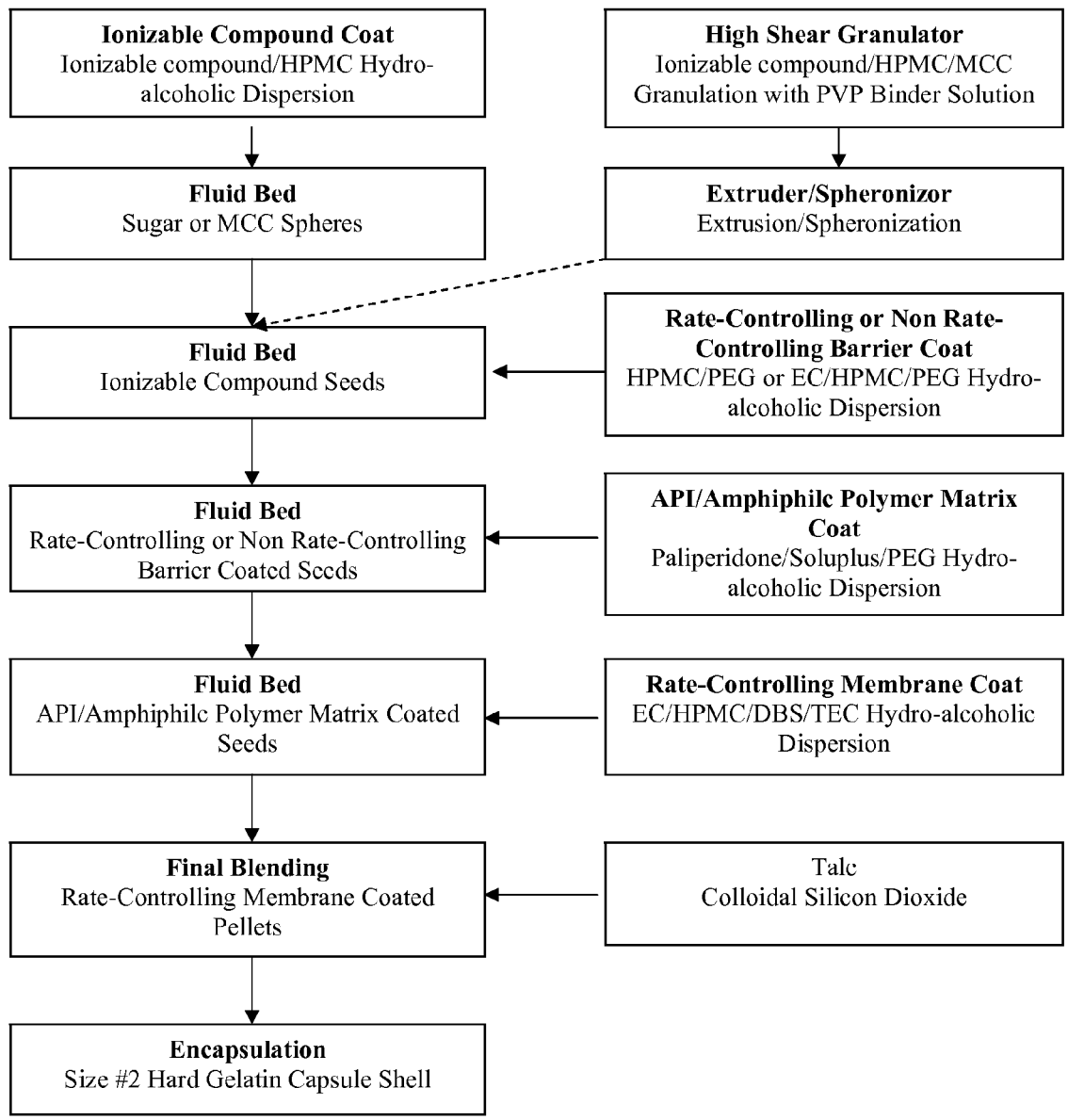
FIG. 4 provides a representative flow chart for making oral dosage forms according to the present invention.
Figure 5:
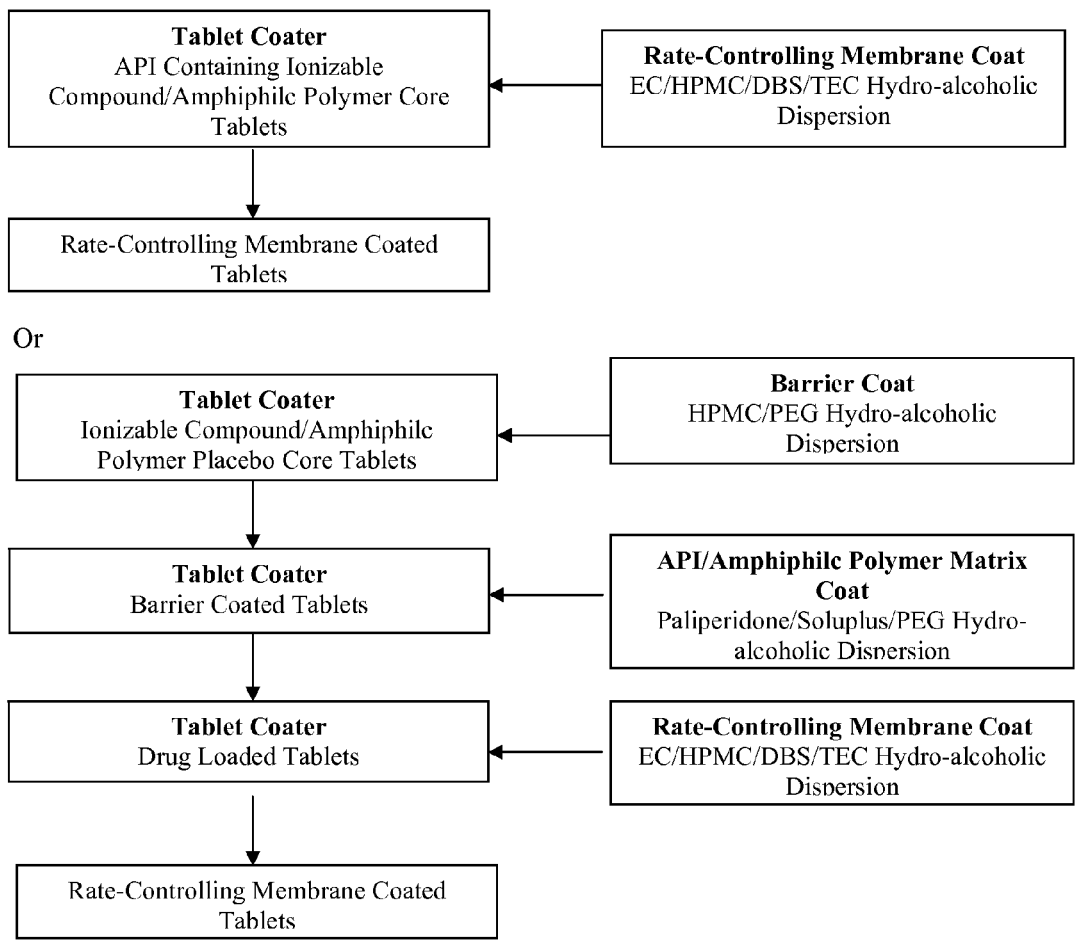
FIG. 5 provides a representative flow chart for making oral dosage forms according to the present invention.
Figure 6:
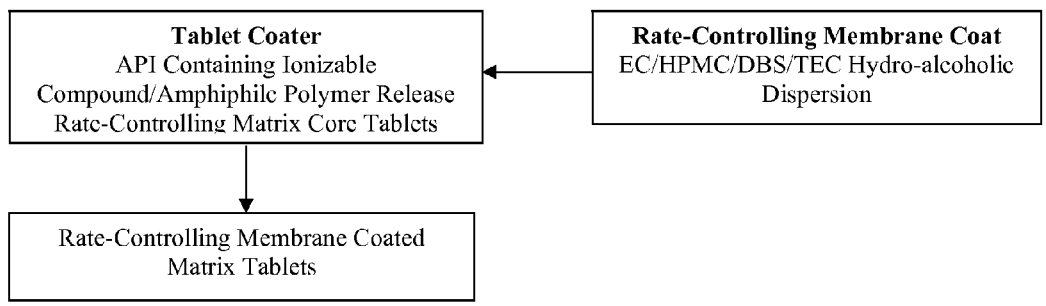
FIG. 6 provides a representative flow chart for making oral dosage forms according to the present invention.
Figure 6:
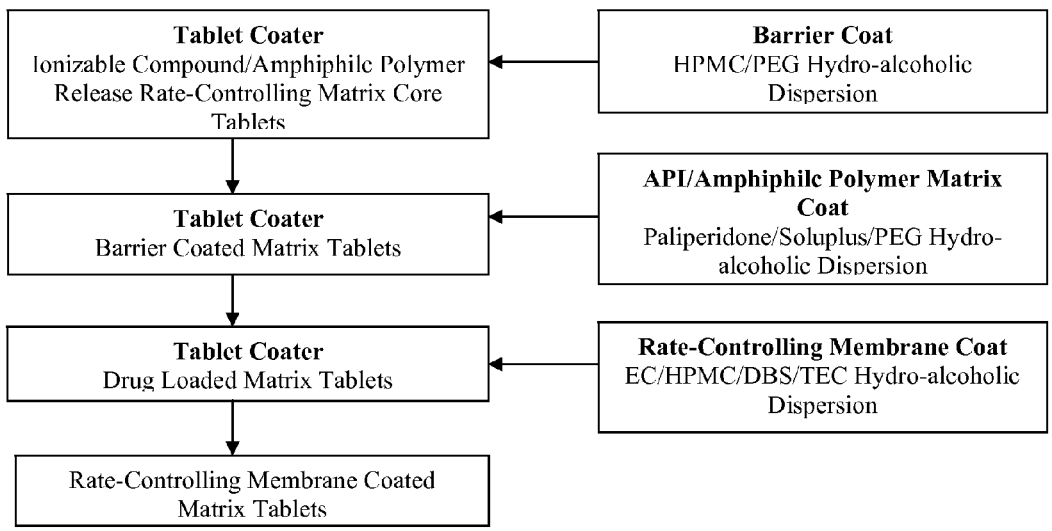

More detailed representative process flowcharts are shown in FIGS. 4-6. In a representative embodiment the dosage form may be a tablet comprising, for example, (a) tartaric acid as the core (b) tartaric acid release rate-controlling barrier coat (c) an API and an amphiphilic polymer, SoluPlus® coat as a layer, and (d) a sustained release/controlled release layer.

The solid oral dosage form referred to in FIG. 4 also may be manufactured using seeds/pellets of an ionizable compound. Such seeds/pellets may be prepared by extrusion-spheronization of the ionizable compound, microcrystalline cellulose and hydrophilic polymers such as hydroxypropyl methyl cellulose, or by layering the ionizable compound onto sugar or microcrystalline cellulose spheres in, for example, a fluid bed coater. Such seeds/pellets may be further coated with a rate-controlling or a non rate-controlling barrier coat comprising hydroxypropyl methyl cellulose, ethyl cellulose, or combinations thereof, in a fluid bed coater. Such coated seeds may be further coated with a mantle comprising a dispersion of API in an amphiphilic polymer, followed by a final coat of rate-controlling membrane. The rate controlling membrane may include ethyl cellulose, hydroxypropyl methyl cellulose, dibutyl sebacate, triethyl citrate, or combinations thereof.

FIG. 5 shows another representative method for making representative dosage forms according to the present invention. As shown in FIG. 5, the solid oral dosage form may be a tablet which may be manufactured by compression of granules prepared by wet granulation. The granules may be prepared by granulating the API, ionizable compound, an amphiphilic polymer, and microcrystalline cellulose along with a binder such as Povidone K90. These granules may be dried, milled and compressed into a tablet. The tablet then may be coated with a drug release rate-controlling membrane which may include ethyl cellulose, hydroxypropyl methyl cellulose, dibutyl sebacate, triethyl citrate, and combinations thereof.

The solid oral dosage form referred to in FIG. 5 also may be prepared by wet granulation of an ionizable compound, an amphiphilic compound, and microcrystalline cellulose along with a binder such as Povidone K90. Such granules may be dried, milled and compressed into a tablet. The tablets then may be coated with a functional or non-functional barrier comprising hydrophilic and/or hydrophobic polymers such as hydroxypropyl methyl cellulose, ethyl cellulose, and combinations thereof. Coated tablets may be further coated with API dispersed in amphiphilic and hydrophilic polymers. Finally, the tablets may be coated with a drug release rate-controlling membrane which may include ethyl cellulose, hydroxypropyl methyl cellulose, dibutyl sebacate, triethyl citrate, and combinations thereof.

The solid oral dosage form referred to in FIG. 6 may include a drug release rate-controlling membrane coated matrix tablet. Such tablet may be manufactured by compression of granules prepared by wet granulation. The granules may be prepared by granulating the API, ionizable compound, amphiphilic polymer, and hydrophobic polymers such as ethylcellulose, using a binder such as Povidone K90. Such granules may be dried, milled and compressed into a drug release rate-controlling matrix tablet. The tablet then may be further coated with a drug release rate-controlling membrane such as ethyl cellulose, hydroxypropyl methyl cellulose, dibutyl sebacate, triethyl citrate, and combinations thereof.

The solid oral dosage form referred to in FIG. 6 also may include drug release rate-controlling membrane coated matrix tablet. Such tablets may be prepared by wet granulation of the ionizable compound, amphiphilic compound, and hydrophobic polymers such as ethylcellulose, using a binder such as Povidone K90. Such granules may be dried, milled and compressed into an ionizable compound release rate-controlling matrix tablet. The tablets then may be coated with a non-functional barrier which may include hydrophilic polymers such as hydroxypropyl methyl cellulose. The coated tablets may be further coated with the API dispersed in amphiphilic and hydrophilic polymers. Finally, the tablets may be coated with a drug release rate-controlling membrane which may include ethyl cellulose, hydroxypropyl methyl cellulose, dibutyl sebacate, triethyl citrate, and combinations thereof.

Example 1

A representative oral dosage form according to the present invention is shown in Table 3 below.

TABLE 3

| Ingredient | Formula A mg per Dose | Formula B mg per Dose |
|---|---|---|
| IONIZABLE COMPOUND SEEDS | Starting seeds: Sugar or MCC spheres | Starting seeds: Extrusion/spherization pellets |
| Sugar or Macrocrystalline Cellulose Spheres | 100 | N/A |
| Macrocrystalline Cellulose (Avicel PH 101) | N/A | 100 |
| Tartaric Acid, Powder | 20 | 20 |
| Hydroxypropyl Methylcellulose (Methocel E5 Premium LV) | 5 | 5 |
| Isopropyl Alcohol, USP* | q.s. | q.s. |
| Purified Water, USP* | q.s. | q.s. |
| BARRIER COAT | Ionizable compound release rate-controlling barrier coat | Non rate-controlling barrier coat |
| Ethylcellulose (Ethocel Standard 10 Premium) | 10 | N/A |
| Hydroxypropyl Methylcellulose (Methocel E5 Premium LV) | 10 | 20 |
| Polyethylene Glycol (Polyglykol 3350) | 5 | 5 |
| Isopropyl Alcohol, USP* | q.s. | q.s. |
| Purified Water, USP* | q.s. | q.s. |
| API/AMPHIPHILIC POLYMER MATRIX COAT | | |
| Paliperidone | 9 | 9 |
| PEG 6000/vinylcaprolactam/vinylacetate (SoluPlus ®) | 20 | 20 |
| Polyethylene Glycol (Polyglykol 3350) | 6 | 6 |
| Isopropyl Alcohol, USP* | q.s. | q.s. |
| Purified Water, USP* | q.s. | q.s. |
| DRUG RELEASE RATE-CONTROLLING MEMBRANE COAT | | |
| Ethylcellulose (Ethocel Standard 10 Premium) | 8 | 8 |
| Hydroxypropyl Methylcellulose (Methocel E5 Premium LV) | 4 | 4 |
| Dibutyl Sebacate | 1.5 | 1.5 |
| Triethyl Citrate | 1.5 | 1.5 |
| Isopropanol Alcohol* | q.s. | q.s. |
| Purified Water* | q.s | q.s |
| FINAL BLENDING | | |
| Talc | 1 | 1 |
| Colloidal Silicon Dioxide, NF | 1 | 1 |
| TOTAL | 202 | 202 |
| Encapsulated into size #2 hard gelatin capsule shell | | |

*Removed during the manufacturing process.

Example 2

A representative oral dosage form according to the present invention is shown in Table 4 below.

TABLE 4

| Ingredient | Formula A mg per Dose | Formula B mg per Dose | Formula C mg per Dose |
| --- | --- | --- | --- |
| IONIZABLE COMPOUND/AMPHIPHILIC POLYMER CORE | API Containing Core | Placebo Core | Placebo Core |
| Donepezil HCl | 23 | N/A | N/A |
| Tartaric Acid, Powder | 50 | 50 | 50 |
| PEG 6000/vinylcaprolactam/vinylacetate (SoluPlus ®) | 50 | 50 | 50 |
| Microcrystalline Cellulose Avicel PH 101 | 71 | 34 | 34 |
| Povidone K90 | 5 | 5 | 5 |
| Purified Water, USP* | q.s. | q.s. | q.s. |
| Magnesium Stearate | 1 | 1 | 1 |
| Core Tablet Total | 200 | 140 | 140 |
| BARRIER COAT | N/A | Ionizable compound release rate-controlling barrier coat | Non rate-controlling barrier coat |
| Hydroxypropyl Methylcellulose (Methocel E5 Premium LV) | N/A | 10 | 20 |
| Ethylcellulose (Ethocel Standard 10 Premium) | N/A | 10 | N/A |
| Polyethylene Glycol (Polyglykol 3350) | N/A | 5 | 5 |
| Isopropyl Alcohol, USP* | N/A | q.s. | q.s. |
| Purified Water, USP* | N/A | q.s. | q.s. |
| API/AMPHIPHILIC POLYMER MATRIX COAT | | | |
| Paliperidone | N/A | 9 | 9 |
| PEG 6000/vinylcaprolactam/vinylacetate (SoluPlus ®) | N/A | 20 | 20 |
| Polyethylene Glycol (Polyglykol 3350) | N/A | 6 | 6 |
| Isopropyl Alcohol, USP* | N/A | q.s. | q.s. |
| Purified Water, USP* | N/A | q.s. | q.s. |
| DRUG RELEASE RATE-CONTROLLING MEMBRANE COAT | | | |
| Ethylcellulose (Ethocel Standard 10 Premium) | 16 | 16 | 16 |
| Hydroxypropyl Methylcellulose (Methocel E5 Premium LV) | 16 | 16 | 16 |
| Dibutyl Sebacate | 4 | 4 | 4 |
| Triethyl Citrate | 4 | 4 | 4 |
| Isopropanol Alcohol* | q.s. | q.s. | q.s. |
| Purified Water* | q.s | q.s | q.s |
| TOTAL | 240 | 240 | 240 |

*Removed during the manufacturing process.

Example 3

A representative compound according to the present invention is shown in Table 5 below.

TABLE 5

| Ingredient | Formula A mg per Dose | Formula B mg per Dose |
|---|---|---|
| IONIZABLE COMPOUND/AMPHIPHILIC POLYMER EXTENDED RELEASE MATRIX CORE | API Containing Core | Placebo Core |
| Donepezil HCl | 23 | N/A |
| Tartaric Acid, Powder | 50 | 50 |
| PEG 6000/vinylcaprolactam/vinylacetate (SoluPlus ®) | 50 | 50 |
| Ethylcellulose (Ethocel Standard 10FP Premium) | 121 | 84 |
| Povidone K90 | 5 | 5 |
| Purified Water, USP* | q.s. | q.s. |
| Magnesium Stearate | 1 | 1 |
| CORE TABLET TOTAL | 250 | 190 |
| BARRIER COAT | | |
| Hydroxypropyl Methylcellulose (Methocel E5 Premium LV) | N/A | 20 |
| Polyethylene Glycol (Polyglykol 3350) | N/A | 5 |
| Isopropyl Alcohol, USP* | N/A | q.s. |
| Purified Water, USP* | N/A | q.s. |
| API/AMPHIPHILIC POLYMER MATRIX COAT | | |
| Paliperidone | N/A | 9 |
| PEG 6000/vinylcaprolactam/vinylacetate (SoluPlus ®) | N/A | 20 |
| Polyethylene Glycol (Polyglykol 3350) | N/A | 6 |
| Isopropyl Alcohol, USP* | N/A | q.s. |
| Purified Water, USP* | N/A | q.s. |
| DRUG RELEASE RATE-CONTROLLING MEMBRANE COAT | | |
| Ethylcellulose (Ethocel Standard 10 Premium) | 20 | 20 |
| Hydroxypropyl Methylcellulose (Methocel E5 Premium LV) | 20 | 20 |
| Dibutyl Sebacate | 5 | 5 |
| Triethyl Citrate | 5 | 5 |
| Isopropanol Alcohol* | q.s. | q.s. |
| Purified Water* | q.s | q.s |
| TOTAL | 300 | 300 |

*Removed during the manufacturing process.

Example 4

A solubility test was performed to quantify the synergistic effects provided by the combination of an ionizable polymer and an amphiphilic compound. In this Example the ionizable compound was citric acid and the amphiphilic compound was SoluPlus®.

TABLE 6

| | Paliperidone Solubility at Room Temperature (mg/ml) |
|---|---|
| Paliperidone in Water | 0.0 |
| Paliperione in 10% Soluplus Aqueous Solution | 0.6 |
| Paliperione in 10% Citric Acid Aqueous Solution | 241.1 |
| Paliperione in 10% Soluplus and 10% Citric Acid Aqueous Solution | 323.8 |

As shown above the solubility of the active compound, the solubility of paliperidone was 34.3% higher in a solution containing an ionizable compound and an amphiphilic polymer compared to a solution containing an ionizable compound without an amphiphilic polymer.

What is claimed is:

1. An extended-release oral dosage form for poorly soluble amine compounds comprising,
   (a) a core having an ionizable compound, wherein the ionizable compound is an organic acid, wherein the organic acid is selected from the group consisting of citric acid, maleic acid and combinations thereof;
   (b) a barrier layer coating the core;
   (c) a mantle of a matrix having a poorly soluble amine compound and at least one amphiphilic polymer, wherein the amphiphilic polymer is selected from the group consisting of polyethylene glycol 6000/vinylcaprolactam/vinyl acetate 13/57/30, d-α-tocopheryl polyethyleneglycol 1000 succinate (Vitamin E-TPGS), and combinations thereof; and
   (d) a release-rate controlling layer coating the mantle;
   wherein the ionizable compound and the amphiphilic polymer are in amounts sufficient to provide synergistic solubility effect.

2. The ectended-release oral dosage form of claim 1, wherein the amphiphilic polymer has an HLB of at least about 7.0.

3. The ectended-release oral dosage form of claim 1, wherein the poorly soluble amine compound is selected from the group consisting of paliperidone, donepezil, tamsulosin, methylphenidate, olanzapine and dipyridamole.

4. The ectended-release oral dosage form of claim 1, wherein the poorly soluble amine compound has a pKa from about 5 to about 11 and a nitrogen content from about 3% to about 23% of the total molecular weight of the poorly soluble amine compound.

5. The ectended-release oral dosage form of claim 1, wherein the poorly soluble amine compound has a pKa from about 8 to about 9 and a nitrogen content from about 8% to about 15% of the total molecular weight of the poorly soluble amine compound.

6. The ectended-release oral dosage form of claim 1, wherein the release-rate controlling layer is selected from the group consisting of hydrophobic polymers selected from ethylcellulose, methylcellulose, propylcellulose, ethylmethylcellulose, cellulose acetate, cellulose acetate propionate or ethyl acrylate-methyl methacrylate copolymer, enteric polymers, methacrylic acid-ethyl acrylate copolymer, methacrylic acid-methyl methacrylate copolymer, hydroxypropyl methylcelluose phthalate, hydroxypropyl methylcellulose acetate succinate, hydrophilic polymers, hydroxypropyl methylcellulose, hydroxypropyl cellulose, povidone, copovidone, polyethylene glycol, triacetin, dibutyl sebacate, triethyl citrate, and combinations thereof.

7. An extended-release oral dosage form for poorly soluble amine compounds comprising,
   (a) a core having an ionizable compound, and a mantle of a matrix having an amphiphilic polymer and a poorly soluble amine compound, wherein the ionizable compound comprises an organic acid,
   wherein the organic acid is selected from the group consisting of citric acid, maleic acid and combinations thereof,
   wherein the amphiphilic polymer is selected from the group consisting of polyethylene glycol 6000/vinylcaprolactam/vinyl acetate 13/57/30, d-α-tocopheryl polyethyleneglycol 1000 succinate (Vitamin E-TPGS), and combinations thereof and the amphiphilic polymer has an HLB of at least about 7.0;

wherein the ionizable compound and the amphiphilic polymer are in amounts sufficient to provide synergistic solubility effect; and (b) a release-rate controlling membrane selected from the group consisting of a hydrophobic polymer, an enteric polymer, a hydrophilic polymer, a plasticizer and combinations thereof, wherein the core is covered by the release-rate controlling membrane.

* * * * *

UNITED STATES PATENT AND TRADEMARK OFFICE
CERTIFICATE OF CORRECTION

PATENT NO.         : 9,011,912 B2
APPLICATION NO.    : 12/900205
DATED              : April 21, 2015
INVENTOR(S)        : Yanming Zu, Sudhir Gorukanti and Salah U. Ahmed It is certified that error appears in the above-identified patent and that said Letters Patent is hereby corrected as shown below:

In the Claims

Column 25, Claim 2, line 1: delete "ectended-release" and insert --extended-release-- therefor.
Column 30, Claim 3, line 1: delete "ectended-release" and insert --extended-release-- therefor.
Column 35, Claim 4, line 1: delete "ectended-release" and insert --extended-release-- therefor.
Column 40, Claim 5, line 1: delete "ectended-release" and insert --extended-release-- therefor.
Column 45, Claim 6, line 1: delete "ectended-release" and insert --extended-release-- therefor.

Signed and Sealed this
Eleventh Day of August, 2015

Michelle K. Lee
*Director of the United States Patent and Trademark Office*